(12) United States Patent
Bigdeli-Issazadeh et al.

(10) Patent No.: US 8,337,505 B2
(45) Date of Patent: Dec. 25, 2012

(54) METHOD FOR COUPLING AN INTRAMEDULLARY NAIL AND ASSOCIATED INSTRUMENTS

(75) Inventors: Sabine Bigdeli-Issazadeh, Felde (DE); Axel Cremer, Wiler b. Utzenstorf (CH)

(73) Assignee: Stryker Trauma GmbH (DE)

( * ) Notice: Subject to any disclaimer, the term of this patent is extended or adjusted under 35 U.S.C. 154(b) by 192 days.

(21) Appl. No.: 12/966,239

(22) Filed: Dec. 13, 2010

(65) Prior Publication Data

US 2011/0078887 A1 Apr. 7, 2011

Related U.S. Application Data

(62) Division of application No. 10/864,039, filed on Jun. 9, 2004, now Pat. No. 7,901,410.

(30) Foreign Application Priority Data

Jun. 11, 2003 (DE) ................................. 203 09 058

(51) Int. Cl.
*A61B 17/58* (2006.01)
*A61B 17/60* (2006.01)
*A61F 2/00* (2006.01)

(52) U.S. Cl. ........................................................ 606/99
(58) Field of Classification Search .............. 606/62–68, 606/99, 86 A, 86 B, 914–916
See application file for complete search history.

(56) References Cited

U.S. PATENT DOCUMENTS

| | | | |
|---|---|---|---|
| 959,226 A | 5/1910 | Keys | |
| 2,444,758 A | 7/1948 | Stillbach | |
| 2,672,861 A | 3/1954 | Salo Jonas et al. | |
| 3,478,302 A | 11/1969 | Chirumbolo | |
| 4,487,469 A | 12/1984 | Bjork | |
| 4,943,182 A | 7/1990 | Hoblingre | |
| 5,156,483 A | 10/1992 | Mangas | |
| 5,176,681 A | 1/1993 | Lawes et al. | |
| 5,226,426 A * | 7/1993 | Yoon | 600/566 |
| 5,308,350 A | 5/1994 | Mikhail | |
| 5,499,986 A | 3/1996 | Dimarco | |
| 6,010,508 A | 1/2000 | Bradley | |
| 6,022,355 A | 2/2000 | Peche et al. | |
| 6,183,477 B1 * | 2/2001 | Pepper | 606/104 |
| 7,175,633 B2 | 2/2007 | Roth et al. | |
| 7,296,804 B2 | 11/2007 | Lechot et al. | |
| 7,338,497 B2 | 3/2008 | Coon et al. | |
| 7,344,565 B2 | 3/2008 | Seyer et al. | |
| 2005/0203520 A1 | 9/2005 | Volzow | |

FOREIGN PATENT DOCUMENTS

| | | |
|---|---|---|
| DE | 19806323 | 2/1998 |
| EP | 0441256 | 2/1991 |
| WO | 03/041595 | 5/2003 |

* cited by examiner

*Primary Examiner* — Sameh Boles
(74) *Attorney, Agent, or Firm* — Lerner, David, Littenberg, Krumholz & Mentlik, LLP

(57) ABSTRACT

A method of connecting an intramedullary nail and a targeting and/or nailing instrument includes engaging a coupling element which has an axially parallel projection with an axially parallel recess on the hollow connection end of the nail. The engagement of the projection and recess fastens the nail under axial engagement on the connection end of the instrument in predefined rotational position on the instrument. A quick-fastener element engages in the connection end of the nail and has a first coupling element and the connection end of the nail has a second coupling element. The coupling elements are configured so that in a first rotational position relative to the axially parallel projection the instrument can be introduced into the connection end of the nail and in a second rotational position the coupling elements cooperate so that the nail is held axially fixedly on the instrument.

14 Claims, 5 Drawing Sheets

METHOD FOR COUPLING AN INTRAMEDULLARY NAIL AND ASSOCIATED INSTRUMENTS

CROSS-REFERENCE TO RELATED APPLICATION

This application is a divisional of U.S. application Ser. No. 10/864,039, filed on Jun. 9, 2004, now U.S. Pat. No. 7,901,410, and the disclosure of which is incorporated herein by reference.

BACKGROUND OF THE INVENTION

The invention relates to a combination comprised of an intramedullary nail and a targeting and/or nailing instrument. More particularly, it relates to a coupling system for quickly connecting an instrument to a bone nail.

Intramedullary nails are generally driven into the intramedullary space using a so-called nailing instrument. The nailing instrument is connected using a suitable connection with the nail before the nail is driven into the bone with the aid of a hammer or the like. In the case of so-called locking nails, which are provided with transverse bore holes for receiving bone or locking screws, a targeting instrument serves also as the nailing instrument. The targeting instrument is connected with the facing end of the bone nail using a clip and a targeting section running parallel to the bone is used for locating the otherwise invisible transverse bore holes of the nail in the bone. For this reason, it is necessary to orient the nail and the targeting device in a predefined rotational position relative to each other. To this end, it is well-known to provide an axially parallel projection at the connection end of the targeting device, which engages in an axially parallel recess. The connection of the connection end of the targeting device with the nail is generally done with the aid of a screw or by using a screw sleeve as disclosed in U.S. Pat. No. 5,176,681. The screw sleeve is used to keep a passage open to the inside of the nail, so that it is possible to introduce or to actuate a locking screw in the nail, while the targeting device is connected with the nail. The locking screw is used to lock a femoral neck screw, which is passed through an inclined transverse bore hole of the nail. The locking screw prevents movement of the neck screw in particular in the direction of rotation, but allows axial movement of the neck screw.

The known system requires setting the nail on the targeting unit manually and at the same time screwing the parts together which is relatively cumbersome for one person acting alone.

BRIEF SUMMARY OF THE INVENTION

Therefore, one aspect of the invention is to simplify handling of the connection between the nail and the targeting and/or nailing instrument.

In the case of the present invention this aspect is achieved with a quick-fastener element rotationally mounted on the connection end of the targeting and/or nailing instrument. The element engages in the hollow connection end of the nail and has a first coupling element. The connection end of the nail has on its inside a second coupling element and the coupling elements are configured, so that in a first rotational position of the quick-fastener element, in which the quick-fastener element has a relative rotational position via-à-vis an axially parallel projection, into which the connection end of the nail can be introduced in a second rotational position of the quick-fastener element. The coupling elements cooperate for holding the nail axially fixed on the targeting and nailing instrument.

When bringing together the nail and the targeting and/or nailing instrument, the nail is on the one hand positioned opposite to the instrument in the correct rotational position, so that the axially parallel projection can engage in an axially parallel recess of the nail. At the same time, the quick-fastener element is rotated into a position, in which it can be introduced into the open end of the nail. Then the quick-fastener element is rotated into its second position, whereby the coupling elements interlock with each other, in order to establish an axial fixation of the nail on the targeting nailing instrument. Rotational fixation is already accomplished virtue of the interlocking of the axially parallel projection of the connection end of the instrument in the axially parallel recess of the nail.

The embodiment according to the invention has the advantage, that fixation of a nail, the targeting and nailing instrument and also the removal thereof is considerably simplified. It is necessary that the nail is appropriately configured at the connection end, whereby a coupling element is created, which cooperates with the coupling element of the quick-fastener element.

Manipulation in the case of the invention is even improved more, if the quick-fastener element is spring biased in the first rotational position towards the second rotational position. The first and second coupling elements are configured, so that they automatically cooperate, when the quick-fastener element is installed axially in the connection end of the nail in a predefined section.

One possible embodiment of the coupling element in the nail resides in that a threaded section is provided in the nail. Further, at least one axially parallel groove is formed in the nail, with which a radial projection of the quick-fastener element cooperates. The projection is introduced into the axially parallel groove of the nail by a predefined distance and then upon rotation of the quick-fastener element cooperates with a thread segment or a groove of the threaded segment. Obviously, the pitch of the threaded segment in the nail is extremely low because the quick-fastener element is mounted preferably axially fixed in the connection end of the targeting and/or nailing instrument. Preferably, three radial projections arranged in 120° intervals are provided on the quick-fastener element, said projections being spaced axially around the thread pitch. The threaded and grooved segment is then so configured that one projection each cooperate with one lead segment of the threaded segment.

According to one embodiment of the invention, the quick-fastener element has a sleeve, which is axially fixedly but limitedly rotatably mounted in a bore hole of the connection end of the targeting and nailing instrument. The sleeve has a radial actuating pin, which extends outwardly through a radial slot in the connection end. It is, in fact conceivable, to use also a cylindrical body as the quick-fastener element instead of a sleeve. The sleeve has the advantage, that using the sleeve, access to the inside of the nail is preserved, for actuation of a locking pin in the nail.

It has already been mentioned that the quick-fastener element can be biased in the direction of rotation. According to one embodiment of the invention, the spring for pre-tensioning the quick-fastener element is a helical spring, which cooperates on the one hand with the sleeve and on the other with the bore hole of the connection end of the instrument.

In order to make possible a reliable contact of the targeting and nailing instrument at the nail, it is advantageous according to a further embodiment of the invention, if the connection end of the targeting and nailing instrument has a sleeve-like end section, which approximately fittingly engages in a corresponding bore hole segment of the connection end of the nail.

These and other aspects of the invention are achieved by a connection system for coupling an instrument to a bone nail. This system includes a bone nail extending along a longitudinal axis and having a proximal end with an internal bore, including at least one slot extending parallel to the axis and at least one groove extending generally perpendicular to the axis intersecting the slot. The connector for coupling the instrument to the nail includes a spring-biased rotatable coupling element having an end for engaging the bore in the nail. The coupling element end includes at least one radially extending pin for engaging the at least one generally perpendicular groove. The coupling element is rotatable from a first position to a second position biased towards the first position wherein the pin on the coupling element is alignable with a slot in the nail in the second position after insertion in the nail end, and can engage the groove in the nail on movement from the second position towards the first position by action of the biasing spring. Preferably, the bone nail has three circumferentially spaced slots and three axially spaced grooves and the coupling element has three pins for respectively engaging the slots and grooves. In the preferred embodiment, the three slots and the three pins are circumferentially spaced at 120°. Also in the preferred embodiment, the coupling element is in the form of a rotatable sleeve mounted in a bore in the connector with a spring mounted between the bore in the connector and the sleeve for biasing the sleeve towards the first position. To facilitate movement of the sleeve within the bore of the connector, a radially extending actuator arm may be provided, which arm extends through a slot in the connector which allows movement of the sleeve from the first position to the second position so that the pins on the sleeves can be aligned with the slots in the end of the bone nail. In order to prevent the relative rotation of the connector and the nail end, an anti-rotation element such as an axial extension from the connector for engagement in the recess in a nail end is provided.

BRIEF DESCRIPTION OF THE DRAWINGS

The present invention will be better understood on reading the following detailed description of non-limiting embodiments thereof, and on examining the accompanying drawings, in which.

DETAILED DESCRIPTION

Figure 1:
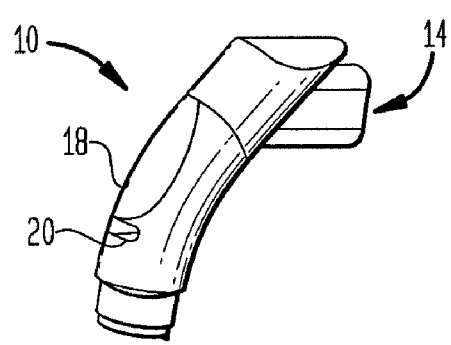
FIG. 1 is a perspective view of the connection end of a targeting and nailing instrument.
Figure 2:
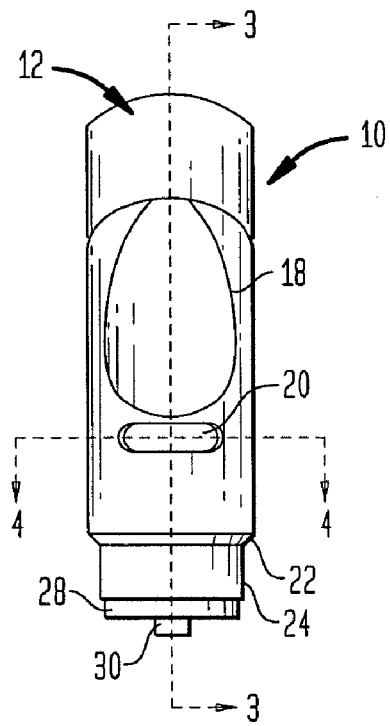
FIG. 2 is an enlarged lateral view of the instrument of FIG. 1.
Figure 3:
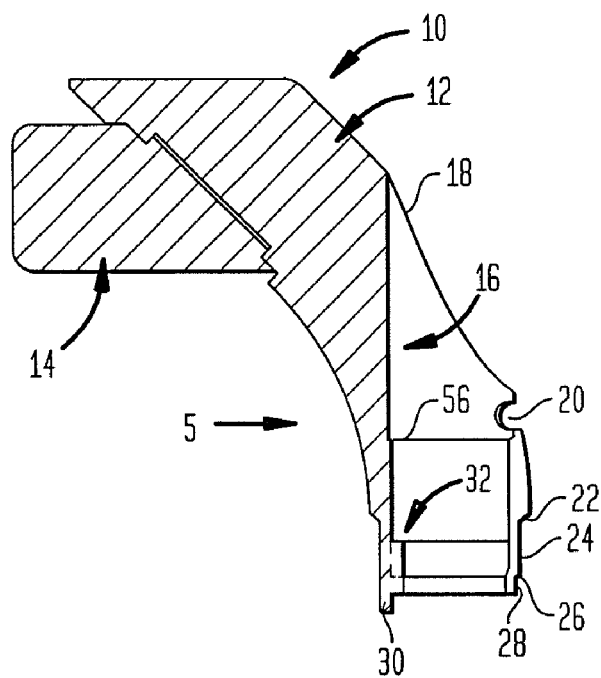
FIG. 3 is a sectional view through the instrument of FIG. 2 along the line 3-3.

FIGS. 1 to 3 represent a connection end 10 of a nailing and targeting instrument which has a targeting portion which is not represented in detail. Connection end 10 has a first part 12 and a second part 14 which, in the preferred embodiment, are bonded together by means of a weld. The part 14 serves as the connection with the other section of the targeting unit (not shown) and which is of no significance for the purposes of the description of the present invention.

Figure 4:
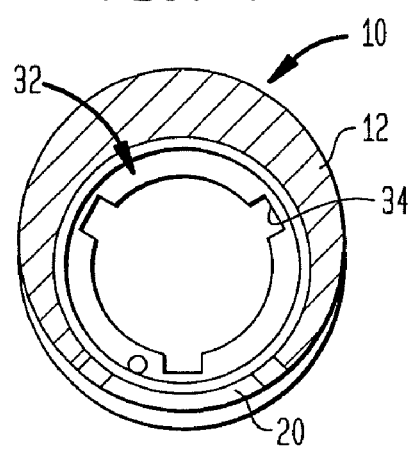
FIG. 4 is a sectional view through the instrument of FIG. 2 along the line 4-4.

In the preferred embodiment, the arcuate, deflected, circular cross-section part 12 has a straight linear bore hole 16, which opens upwardly into an inclined opening 18. A short distance below the opening 18 a radial slot 20 is formed in the part 12; a conical step 22 is situated underneath the slot 20 and step 22 is a cylindrical section 24. The cylindrical section 24 transitions over a further radial step 26 into a cylindrical section 28 which has a smaller diameter than section 24. An axially parallel projection 30 connects to section 28. On the inside of the bore hole 16, at the level of the cylindrical section 24, there is a radial flange 32 oriented inwardly, which, as can be seen in FIG. 4 has three radial recesses 34 arranged at 120° intervals.

Figure 5:
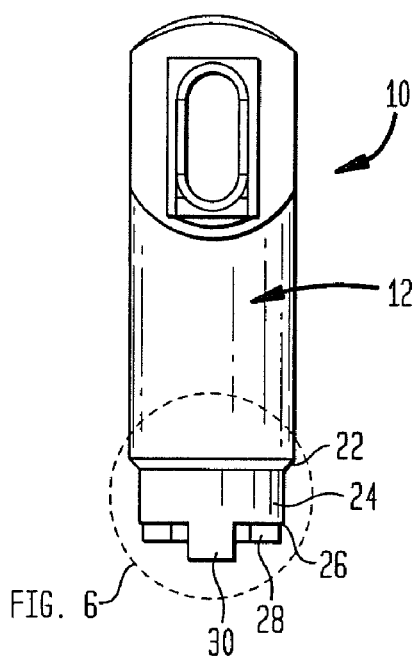
FIG. 5 is a lateral view of the instrument viewed from arrow 5 of FIG. 3.
Figure 6:
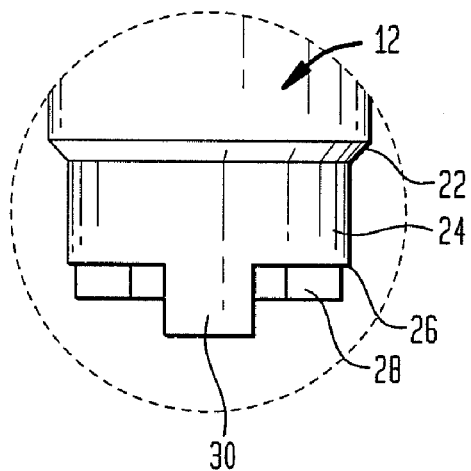
FIG. 6 is an enlargement of the area of FIG. 5 in circle 6.
Figure 7:
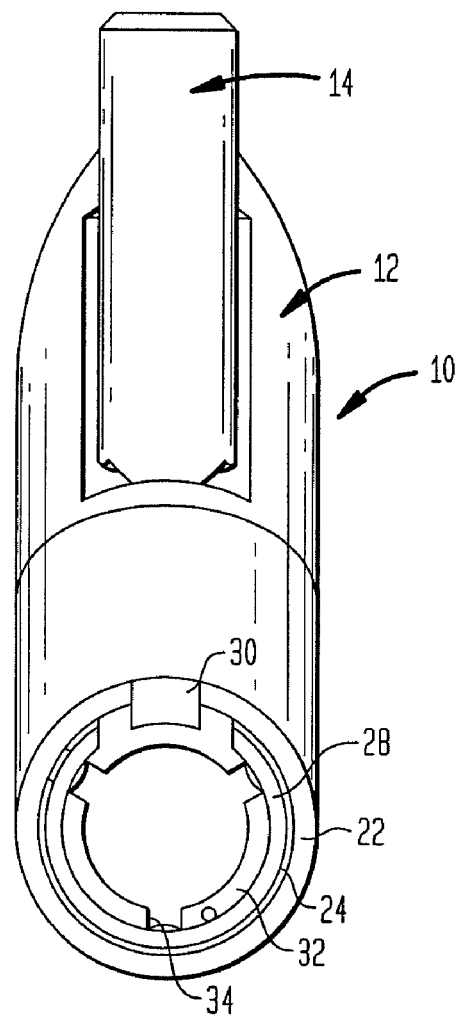
FIG. 7 is a bottom view of the instrument according to FIG. 3 or FIG. 5.

FIGS. 5 and 7 show that the external diameter of the axially parallel projection 30 corresponds to the diameter of cylindrical section 24. In the preferred embodiment, section 28 ends on both sides of the projection 30 at a distance from the projection (as can be seen especially in FIG. 7).

Figure 12:
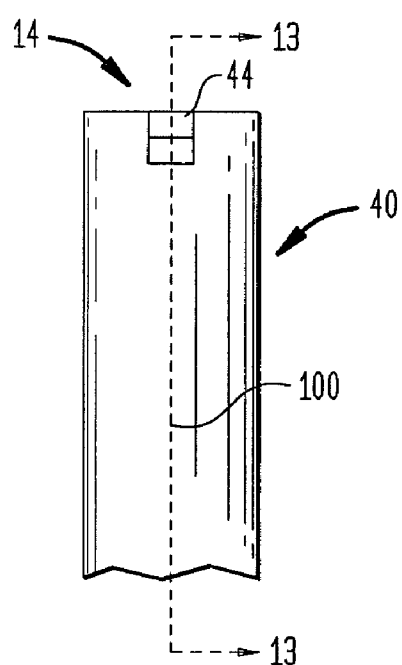
FIG. 12 is the connection end of a locking nail (partially shown)

In the preferred embodiment, an upper nail section 40 is shown in FIGS. 12 to 15. It is part of a cylindrical nail shaft, which has an axial bore hole 42. As can be seen in FIG. 12, the nail section 40 has a recess 44 parallel to the nail axis 100 at its upper end. The bore hole 42 has an upper enlarged portion 43 and at the upper end a bore hole section 46 is provided. The internal diameter of the bore hole section 46 corresponds to the external diameter of cylindrical section 28 of the connection end of the instrument 10. The connection end can therefore be inserted with the section 28 into the bore hole section 46, wherein the axially parallel projection 30 engages appropriately in the recess 44. In the preferred embodiment, the external diameter of nail section 40 corresponds to the external diameter of section 24 of the connection end of instrument 10.

Figure 8:
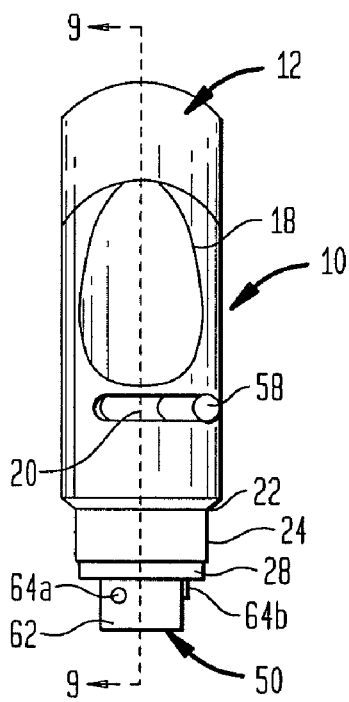
FIG. 8 is a view similar to that of FIG. 2 but with an installed quick-fastener element.
Figure 9:
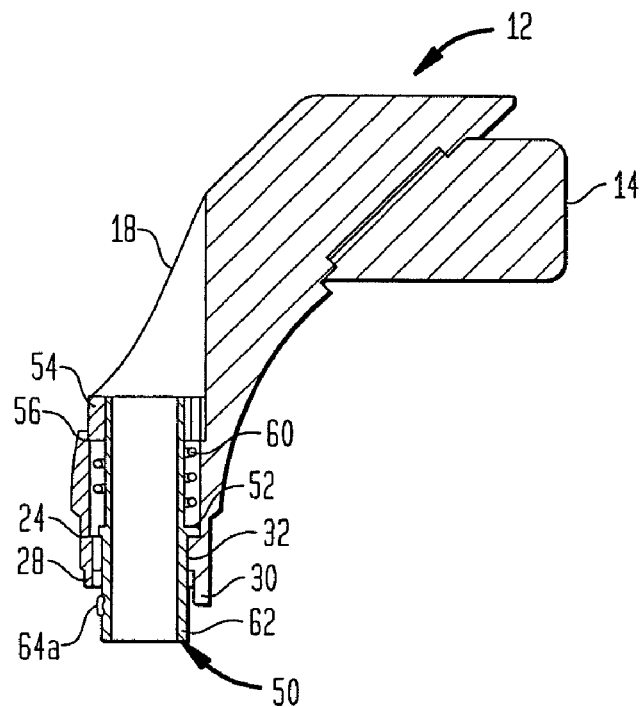
FIG. 9 is a sectional view through FIG. 8 along line 9-9.

FIGS. 8 to 11 show a quick-fastener inserted into the connection end of the instrument. The preferred quick-fastener is a sleeve 50, which is inserted into the bore hole 16 of the part 12. Sleeve 50 has a radial flange 52, which cooperates with a collar which is formed by the radial flange 32. In the axial space above radial flange 52, sleeve 50 has at its upper left end (as shown in FIG. 9) a further radial flange 54, which can engage a recessed surface 56 for attachment. An actuation pin 58 is compressed radially in a bore hole 55 of the flange 54. Pin 58 extends through the radial slot 20. An annular space in which a helical spring 60 is arranged is formed between sleeve 50 and the bore hole section between the recess 56 and the flange 32. The one end of the helical spring is fixedly connected to the part 12 and the other end is connected to the sleeve 50. A rotation of sleeve 50 therefore results in a pretensioning of sleeve 50 by spring 60.

Figure 11:
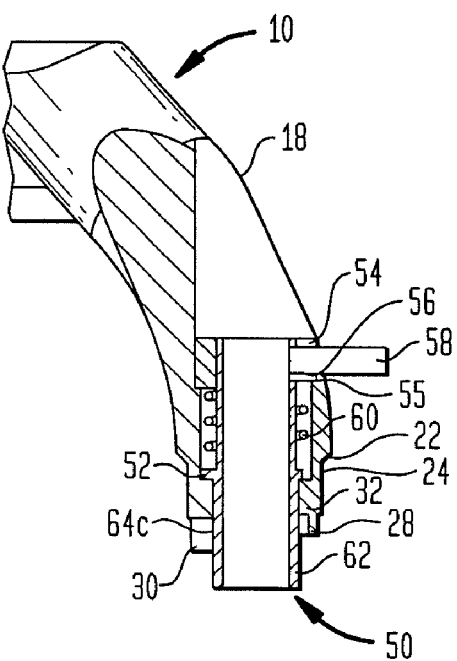
FIG. 11 is a sectional view through FIG. 10 along the line 11-11.

As can be seen in FIGS. 8, 9 and 11, in the installed position, the sleeve 50 projects downwardly. As can be seen further in these figures, the overhanging sleeve section 62 is provided with short radial studs 64. In total, in the preferred embodiment, three studs 64 are arranged in peripheral intervals of 120° and are preferably axially spaced as well. This spacing will be explained in more detail below.

Figure 13:
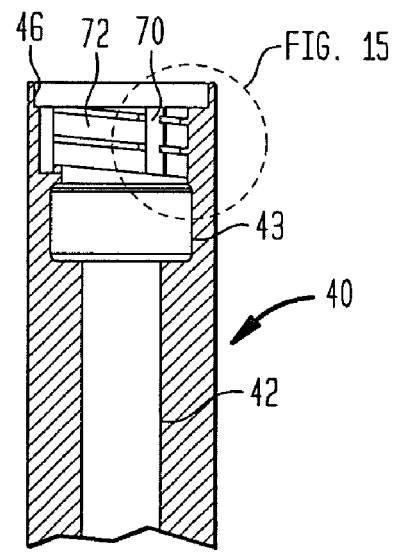
FIG. 13 is a sectional view through the nail according to FIG. 12 along the line 13-13.
Figure 14:
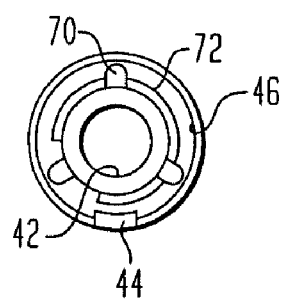
FIG. 14 is an end view of the nail according to FIG. 12 in the direction of the arrow 14.
Figure 15:
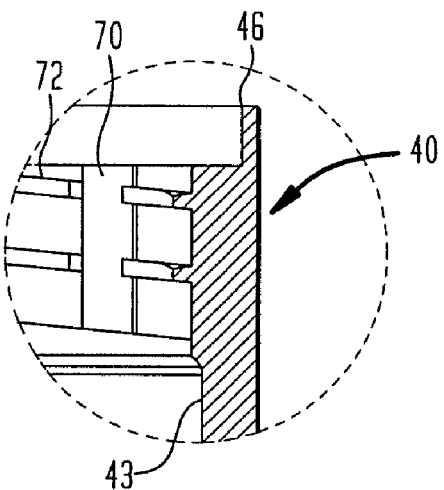
FIG. 15 represents an enlargement of area 14 according to FIG. 13.

It can be clearly seen in FIGS. 13 to 15, that below bore hole section 46 three axially parallel grooves are formed in the wall of the nail section 40. These are indicated by reference 70. Grooves 70 interrupt a thread section 72, which is formed below bore hole section 46. The pitch of this thread is extraordinarily flat. Each groove 70 cooperates with a pin 64 upon assembly of nail 40 and connection end 10.

Figure 10:
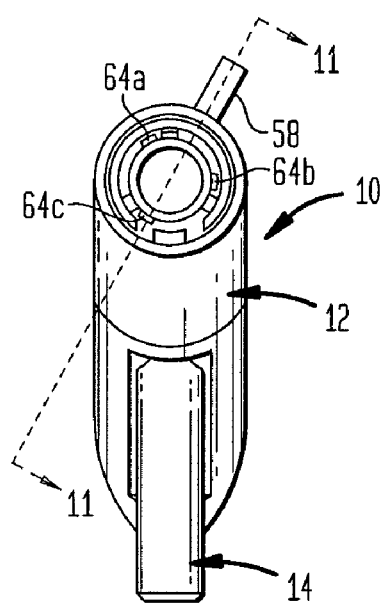
FIG. 10 is a top view of the instrument of FIG. 8 or 9.
Figure 16:
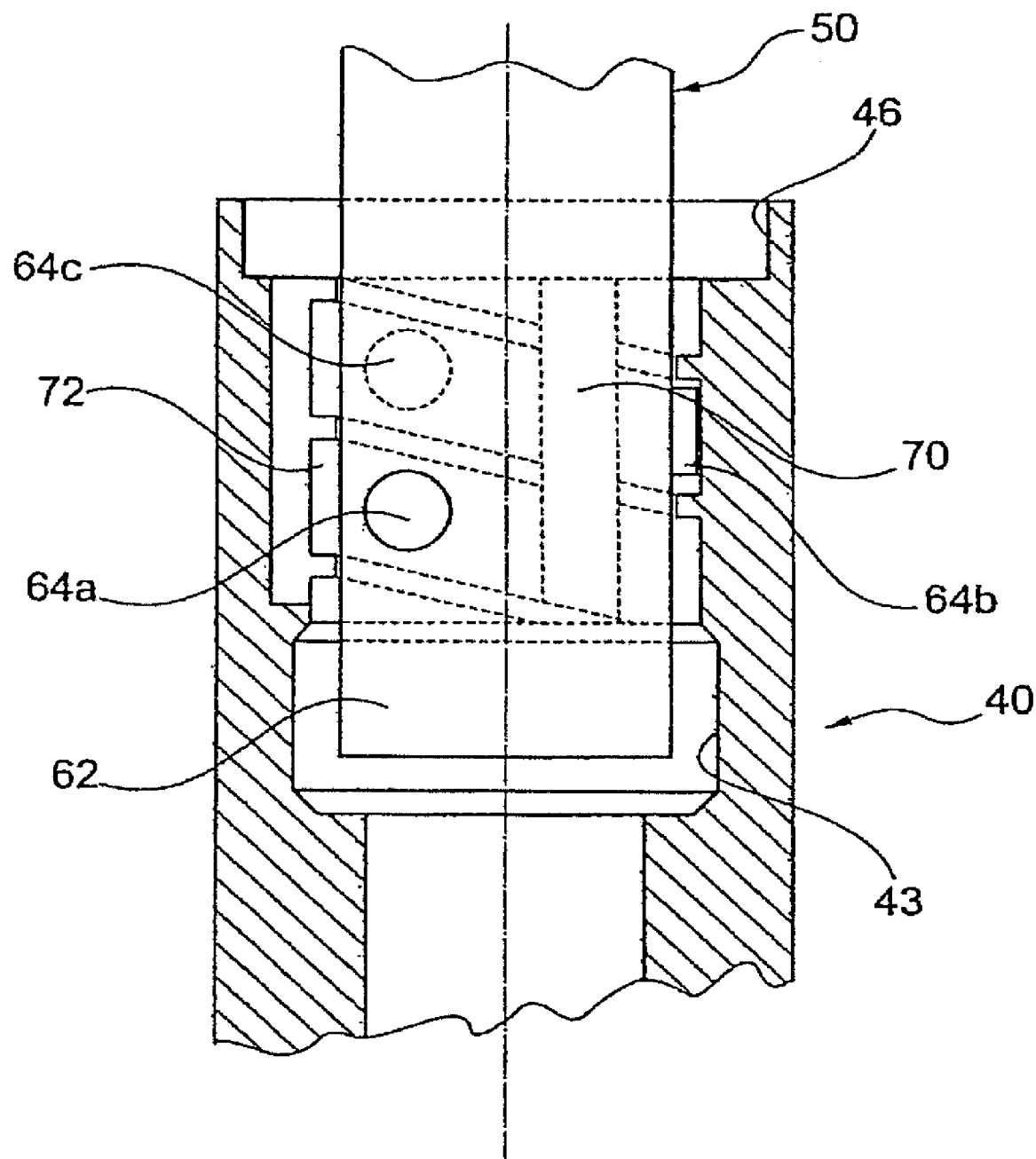
FIG. 16 is a partial cross-sectional view of the sleeve shown in FIGS. 8 and 9 inserted into the nail end of FIGS. 13 and 15.

As can be seen in FIG. 10, the three radial projections or studs 64a, b and c are oriented at 120° and are axially offset around the threaded circumference of nail end portion 43 as shown in FIG. 16.

If, as described above, connection end 10 is inserted into nail section 40, in which cylindrical section 28 engages in bore hole section 46 and projection 30 in the recess 44, then this can be accomplished only if, in addition, sleeve 50 has a rotational position, so that one stud 64 can be introduced into each groove 70. In order to achieve this rotational positioning, sleeve 50 must be correspondingly rotated; that is, with the aid of actuation pin 58. With this rotation, the helical spring 60 is tensioned. If, in the described arrangement of the parts, the nail is completely pushed in using part 12 of the connection end 10, the pins 64 are oriented towards a thread lead of the thread section 72 or towards a thread groove. The axial spacing of studs 64 is such, that it corresponds to the pitch of thread section 72. If now, in the described arrangement of the parts, actuation pin 58 is released, the sleeve 50 is urged by the spring 60 to rotate back into the unstressed or less stressed position, whereby the studs 64 engage into each one groove section of the thread section 72 and thereby establish a locking with the nail section 40. In this fashion, the nail section 40 is affixed both in the direction of rotation and axially securing to the connection end 10 of the instruments.

An alternative attachment of the nail section 40 to the instrument 10 is done as follows. The nail end 40 is pushed over the projecting sleeve section 62, whereby the studs 64 engage in the grooves or slots 70. Then the nail section 40 is rotated relative to the instrument 10, until the projection 30 is aligned with the recess 44 of the nail section. After this alignment, the nail is pushed farther forward against the instrument 10, so that the projection 30 engages completely in the recess 40. As soon as this is completed, the studs 64 are in alignment with the groove sections of the thread section 72 and move automatically into same, because with the described rotating the helical spring 60 was pre-stressed and attempts to rotate the sleeve 50 back into the unrotated direction.

This explanation makes clear that in the described figures a quick-fastener is shown with which the nail, a locking nail, for example, can be connected using a targeting and/or nailing instrument quickly without the assistance of instruments or a screw or the like.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method for connecting an instrument to a bone nail comprising: providing a bone nail having an internal bore at a first end with a circumferential groove within the bore and a slot extending parallel to an axis of the nail intersecting said groove;
providing an instrument for connecting to the nail comprising a spring-biased coupling element having a first end with a radially extending locking pin, said instrument having an elongated opening extending perpendicular to an axis of the instrument from an inner surface to an outer surface of the instrument, said coupling element having a radially extending actuating pin for extending through the elongated opening of said instrument; said coupling element having a first position and a second position wherein the coupling element is spring-biased towards said first position, wherein the coupling element and the first end of said nail includes an operatively engageable anti-rotation means for preventing rotation of the instrument with respect to the nail while allowing rotation of the coupling element; rotating said coupling element against said spring-bias to the second position by actuating said actuating pin of said coupling element within said elongated opening of said instrument; aligning said locking pin on said coupling element with the slot in said nail; inserting the coupling element into said bore in said nail, with said locking pin engaging said slot to an axial position where said locking pin is aligned with said groove; and releasing said actuating pin of said coupling element so that the coupling element rotates towards said first position under force of the spring and said locking pin engages said groove.

2. The method as set forth in claim 1 wherein said coupling element is a sleeve.

3. The method as set forth in claim 1 wherein said internal bore has three slots and three grooves.

4. The method as set forth in claim 3 wherein the spring biased coupling element has three radially extending locking pins.

5. The method as set forth in claim 3 wherein said slots and locking pins are located at 120° intervals.

6. A method for connecting a nailing instrument to a bone nail comprising: obtaining said bone nail extending along a first longitudinal axis and having a proximal end with an internal bore including at least one slot extending axially parallel to the first longitudinal axis and at least one groove extending generally in a plane transverse to the longitudinal axis intersecting said slot; obtaining said nailing instrument for coupling to said proximal end of the nail, the nailing instrument having a bore extending along an axis directed towards the nail, the bore of the nailing instrument having an open first end, and a connector at a second end for coupling the instrument to the nail, and an elongated opening extending perpendicular to the axis from an inner surface of the bore to an outer surface of the nailing instrument, the elongated opening located on the outer surface between the open first end and the connector, the connector comprising a spring-biased rotatable coupling element having an end for engaging said bore in said bone nail, the coupling element being in the form of a rotatable sleeve mounted in the bore of the nailing instrument and a spring mounted between the bore and said rotatable sleeve, the spring biases the sleeve towards a first position wherein the sleeve further comprises a radially extending actuating pin for extending through the elongated opening, an end of said coupling element including at least one radially extending locking pin for engaging said at least one groove; rotating the sleeve mounted in the bore against spring force by actuating the radially extending actuating pin of the coupling element to a second position where the at least one radially extending locking pin is aligned with the axially parallel slot in the internal bore of said nail; inserting the coupling element into the internal bore with the radially extending locking pin sliding down the slot into alignment with the at least one groove in the internal bore; and releasing the sleeve so that the radially extending locking pin rotates towards the first position in the at least one groove by the spring.

7. The method as set forth in claim 6 wherein internal bore has three circumferentially spaced slots and three axially spaced grooves and said coupling element has three axially and circumferentially spaced locking pins for respectively engaging said slots and grooves.

8. The method as set forth in claim 7 wherein said three slots and said three locking pins are circumferentially spaced at 120°.

9. The method as set forth in claim 6 wherein the actuating pin is rotated from a first end position in the elongated opening in the outer surface of the nailing instrument to a second end position in the elongated opening to rotate the sleeve against the spring force and align the radially extending locking pin with the axial nail slot.

10. The method as set forth in claim 9 further comprising releasing the coupling element from the bone nail by moving the actuating pin from the first end position to the second end position within the elongated opening in the nailing instrument.

11. A method for connecting a nailing instrument to a bone nail comprising: obtaining said bone nail having a longitudinal axis and a connection end with a bore including three axially extending slots and three axially spaced grooves extending transverse to the longitudinal axis of the nail, each groove intersecting at least one slot; obtaining said nailing instrument having an axially extending bore and a rotatable coupling element mounted at a connection end of the nailing instrument, the coupling element including three circumferentially and axially spaced radially extending locking pins, alignable with the slots and grooves in the bone nail, said nailing instrument having an elongated opening extending perpendicular to said axially extending bore from an inner surface of said axially extending bore to an outer surface of the nailing instrument, said coupling element having a radially extending actuating pin for extending through the elongated opening of said nailing instrument; the coupling element biased towards a first rotational position with respect to the nailing instrument by a spring element connecting the nailing instrument to the bone nail by inserting the connection end of the nailing instrument into the bore at the connection end of the bone nail and rotating the coupling element against bias of the spring element by actuating said actuating pin to a second position where the three circumferentially and axially spaced locking pins are aligned with the three axially extending slots in the nail; and moving the nailing instrument axially towards the bone nail until the radially extending locking pins are each aligned with a groove and thereafter releasing the actuating pin to allow the spring bias to move the radially extending locking pins towards the first rotational position, wherein a means is provided for preventing rotation of the nailing instrument with respect to the bone nail while allowing rotation of the coupling element.

12. The method as set forth in claim 11 wherein the spring element is a helical spring located between an inner surface of the bore in the nailing instrument and an outer surface of the coupling element.

13. The method as set forth in claim 11 wherein the groove in the bone nail are angled with respect to the longitudinal axis such that the rotation of the coupling element from the second position towards the first position locks the nailing instrument to the bone nail.

14. The method as set forth in claim 11 wherein the radially extending locking pins of the coupling element and the slots in the bone nail are circumferentially spaced at 120°.

\* \* \* \* \*

UNITED STATES PATENT AND TRADEMARK OFFICE
CERTIFICATE OF CORRECTION

PATENT NO. : 8,337,505 B2
APPLICATION NO. : 12/966239
DATED : December 25, 2012
INVENTOR(S) : Sabine Bigdeli-Issazadeh and Axel Cremer Page 1 of 1

It is certified that error appears in the above-identified patent and that said Letters Patent is hereby corrected as shown below:

In the Specification:

Column 2, line 19, before "that fixation" delete ","
Column 2, line 20, replace "is" with --are--
Column 2, line 26, after "more" delete ","
Column 2, line 26, replace "spring biased" with --spring-biased--
Column 2, line 28, after "configured" delete ","
Column 2, line 29, after "cooperate" delete ","
Column 2, line 47, replace "cooperate" with --cooperates--
Column 2, line 50, after "sleeve" delete ","
Column 2, line 53, after "pin" delete ","
Column 2, line 54, after "in fact" insert --,--
Column 2, line 54, after "conceivable" delete ","
Column 5, line 34, after "such" delete ","
Column 5, line 54, replace "was" with --is--

In the Claims:

Column 6, line 20, replace "includes" with --include--
Column 6, line 39, replace "spring biased" with --spring-biased--
Column 7, line 14, after "and" insert --the--
Column 8, line 30, replace "groove" with --grooves--

Signed and Sealed this
Thirty-first Day of March, 2015

Michelle K. Lee
*Director of the United States Patent and Trademark Office*